United States Patent [19]

Wolfram

[11] Patent Number: 4,544,505
[45] Date of Patent: Oct. 1, 1985

[54] PREPARATION OF HALO-α-KETO-CARBOXYLIC ACIDS

[75] Inventor: Joachim W. Wolfram, Baton Rouge, La.

[73] Assignee: Ethyl Corporation, Richmond, Va.

[21] Appl. No.: 544,127

[22] Filed: Oct. 21, 1983

[51] Int. Cl.$^4$ .............................................. C11C 1/00
[52] U.S. Cl. ..................................... 260/413; 562/520
[58] Field of Search ........................ 562/520; 260/413

[56] References Cited

U.S. PATENT DOCUMENTS 4,152,352  5/1979  Perron ................................. 562/406

FOREIGN PATENT DOCUMENTS 2026478  2/1980  United Kingdom .

OTHER PUBLICATIONS

J. Electroanalytical Chemistry, 232, pp. 59-70, (1982).
Rodd, The Chemistry of Carbon Compounds, vol. 1, pp. 226-229 (1952).

Primary Examiner—Helen M. S. Sneed
Attorney, Agent, or Firm—Donald L. Johnson; John F. Sieberth; John F. Hunt

[57] ABSTRACT

Halo-α-keto-carboxylic acids are prepared by reacting a dihaloalkane in a liquid solvent medium with carbon monoxide at elevated temperature and pressure in the presence of a catalytic amount of a metal carbonyl compound and an alkali metal inorganic base or an alkaline earth metal inorganic base.

18 Claims, No Drawings

1

PREPARATION OF HALO-α-KETO-CARBOXYLIC ACIDS

TECHNICAL FIELD

The present invention relates to a process for the bis-carbonylation of a dihaloalkane to form a halo-α-keto-carboxylic acid as the predominant product.

The practical value of such acids and their derivatives is that they can be used in the synthesis or pharmaceuticals, specialty chemicals, amino acids and for preparing polymers.

BACKGROUND OF THE INVENTION

The preparation of α-keto-carboxylic acids and their derivatives has been the subject of a large number of investigations. According to Rodd, *The Chemistry of Carbon Compounds* (1952 edition), Vol. 1, pages 227–229, the following methods of preparation are available:

gentle oxidation of α-hydroxyacids containing a secondary hydroxyl group, or by the enzymatic deamination of α-amino-acids;
hydrolysis of an acyl cyanide;
hydrolysis of α-oximino-esters;
from glycidic acid esters on treatment with benzene saturated with boron trifluoride;
from αβ-dibromocarboxylic acids by forming a piperidine addition compound followed by hydrolysis;
from α-keto-acetals by ultraviolet irradiation in the presence of N-bromosuccinimide;
from α-bromomethylketones by boiling with selenium dioxide in absolute methanol or ethanol;
from carboxylic acid esters by oxidation with selenium dioxide;
permanganate oxidation of vinyl ketones;
from carboxylic acid esters by condensation with oxalic ester followed by decarboxylation;
from aldehydes via 5-alkylidene-2-thio-oxazolid-4-ones or by reaction with methyl methoxyacetate;
hydrolysis of azlactones or acetamido-acrylic acids;
hydrolysis of the reaction product of Grignard reagents on diethyl-oxamic ester;
oxidation of α-hydroxyacid esters containing two β-hydrogen atoms by N-bromosuccinimide in carbon tetrachloride to β-bromo-α-keto-acid esters; and by the action of alkali on the dimethanesulphonates and ditoluene-p-sulphonates of α,β-dihydroxycarboxylic acids.

In co-pending U.S. application, Ser. No. 353,473, entitled "PROCESS FOR PREPARING ALKYL α-KETO-CARBOXYLIC ACIDS FROM ALKYL HALIDES", filed Mar. 1, 1982, now abandoned, there is disclosed a method of preparing certain alkyl α-keto-carboxylic acids by reacting a primary alkyl halide in a liquid solvent medium with carbon monoxide in the presence of a metal carbonyl compound and an alkali metal inorganic base or an alkaline earth metal inorganic base. Further, in co-pending U.S. application, Ser. No. 405,817, entitled "PROCESS FOR PREPARING β-SUBSTITUTED-α-KETO-CARBOXYLIC ACIDS", filed Aug. 6, 1982, there is disclosed the preparation of β-substituted-α-keto-carboxylic acids by reacting a secondary alkyl halide in a liquid solvent medium with carbon monoxide in the presence of a metal carbonyl compound and an alkali metal inorganic base or an alkaline earth metal inorganic base. Still further, in co-pending U.S. application, Ser. No. 405,816, entitled "PREPARATION OF CYCLIC-KETO-ACIDS", filed Aug. 6, 1982, Pat. No. 4,473,706 there is disclosed a method of preparing certain cyclic-keto-acids by reacting a 1-bromoalkane in a liquid solvent medium with carbon monoxide in the presence of a metal carbonyl compound and an alkali metal inorganic base or an alkaline earth metal inorganic base. In co-pending U.S. application, Ser. No. 419,758, entitled "PREPARATION OF 6-CARBOXY-3,4-DIHYDRO-2H-PYRAN", filed on Sept. 20, 1982, abandoned, there is disclosed a process for preparing 6-carboxy-3,4-dihydro-2H-pyran by reacting a 1,4-dihalobutane in a liquid solvent medium with carbon monoxide in the presence of a metal carbonyl compound and an alkali metal inorganic base or an alkaline earth metal inorganic base. And, in co-pending U.S. application, Ser. No. 430,152, entitled "PREPARATION OF BIS-α-KETO-CARBOXYLIC ACIDS," filed Sept. 30, 1982, there is disclosed a process for preparing bis-α-keto acids by reacting a dihaloalkane in a liquid solvent medium with carbon monoxide at elevated temperature and pressure in the presence of a metal carbonyl compound and an alkali metal base or an alkaline earth metal base.

THE INVENTION

It has now been found that halo-α-keto-carboxylic acids of the general formula:

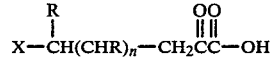

in which R represents hydrogen or an alkyl radical which can be either straight chain or branched containing from about 1 to about 25 carbon atoms and n is 4 to 40, can be prepared by carbonylating a dihaloalkane of the general formula:

wherein R and n are as defined above and X is the same or different and is halogen selected from either chlorine, bromine or iodine, in a liquid solvent medium, with carbon monoxide at a pressure of from about 300 to 3000 psig in the presence of a catalytic amount of a metal carbonyl compound and an alkali metal inorganic base or an alkaline earth metal inorganic base.

The dihaloalkane reactants suitable for use in the present process are well known in the art as are methods for their preparation, and as defined above, are of the general formula:

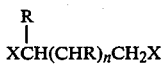

wherein R, n and X are as defined above. A few exemplary materials of this type include:
1,7-dibromoheptane;
1,8-dibromooctane;
1,9-dibromononane;
1,10-dibromodecane;
1,11-dibromoundecane;
1,12-dibromododecane;
1,13-dibromotridecane;

1,14-dibromotetradecane;
1,15-dibromopentadecane;
1,16-dibromohexadecane;
1,17-dibromoheptadecane;
1,18-dibromooctadecane;
1,19-dibromononadecane;
1,20-dibromoeicosane;
1,21-dibromoheneicosane;
1,22-dibromodocosane;
1,23-dibromotricosane;
1,24-dibromotetracosane;
1,25-dibromopentacosane;
1,30-dibromotriacontane;
1,40-dibromotetracontane;
1,7-dichloroheptane;
1,8-dichlorooctane;
1,9-dichlorononane;
1,10-dichlorodecane;
1,11-dichloroundecane;
1,12-dichlorododecane;
1,13-dichlorotridecane;
1,14-dichlorotetradecane;
1,15-dichloropentadecane;
1,16-dichlorohexadecane;
1,17-dichloroheptadecane;
1,18-dichlorooctadecane;
1,19-dichlorononadecane;
1,20-dichloroeicosane;
1,21-dichloroheneicosane;
1,22-dichlorodocosane;
1,23-dichlorotricosane;
1,24-dichlorotetracosane;
1,25-dichloropentaconsane;
1,30-dichlorotriacontane;
1,40-dichlorotetracontane;
1,7-diiodoheptane;
1,8-diiodooctane;
1,9-diiodononane;
1,10-diiododecane;
1,11-diiodoundecane;
1,12-diiodododecane;
1,13-diiodotridecane;
1,14-diiodotetradecane;
1,15-diiodopentadecane;
1,16-diiodohexadecane;
1,17-diiodoheptadecane;
1,18-diiodooctadecane;
1,19-diiodononadecane;
1,20-diiodoeiconsane;
1,21-diiodoheneicosane;
1,22-diiododocosane;
1,23-diiodotricosane;
1,24-diiodotetracosane;
1,25-diiodopentaconsane;
1,30-diiodotriacontane;
1,40-diiodotetracontane;
1-chloro-7-bromoheptane;
1-chloro-8-bromooctane;
1-chloro-9-bromononane;
1-chloro-10-bromodecane;
1-chloro-11-bromoundecane;
1-chloro-12-bromododecane;
1-chloro-13-bromotridecane;
1-chloro-14-bromotetradecane;
1-chloro-15-bromopentadecane;
1-chloro-16-bromohexadecane;
1-chloro-17-bromoheptadecane;
1-chloro-18-bromooctadecane;
1-chloro-19-bromononadecane;
1-chloro-20-bromoeicosane;
1-chloro-21-bromoheneicosane;
1-chloro-22-bromodocosane;
1-chloro-23-bromotricosane;
1-chloro-24-bromotetracosane;
1-chloro-25-bromopentacosane;
1-chloro-30-bromotriacontane;
1-chloro-40-bromotetracontane;
1-chloro-7-chloroheptane;
1-chloro-8-chlorooctane;
1-chloro-9-chlorononane;
1-chloro-10-chlorodecane;
1-chloro-11-chloroundecane;
1-chloro-12-chlorododecane;
1-chloro-13-chlorotridecane;
1-chloro-14-chlorotetradecane;
1-chloro-15-chloropentadecane;
1-chloro-16-chlorohexadecane;
1-chloro-17-chloroheptadecane;
1-chloro-18-chlorooctadecane;
1-chloro-19-chlorononadecane;
1-chloro-20-chloroeicosane;
1-chloro-21-chloroheneicosane;
1-chloro-22-chlorodocosane;
1-chloro-23-chlorotricosane;
1-chloro-24-chlorotetracosane;
1-chloro-25-chloropentaconsane;
1-chloro-30-chlorotriacontane;
1-chloro-40-chlorotetracontane;
1-chloro-7-iodoheptane;
1-chloro-8-iodooctane;
1-chloro-9-iodononane;
1-chloro-10-iododecane;
1-chloro-11-iodoundecane;
1-chloro-12-iodododecane;
1-chloro-13-iodotridecane;
1-chloro-14-iodotetradecane;
1-chloro-15-iodopentadecane;
1-chloro-16-iodohexadecane;
1-chloro-17-iodoheptadecane;
1-chloro-18-iodooctadecane;
1-chloro-19-iodononadecane;
1-chloro-20-iodoeicosane;
1-chloro-21-iodoheneicosane;
1-chloro-22-iodododocosane;
1-chloro-23-iodotricosane;
1-chloro-24-iodotetracosane;
1-chloro-25-iodopentacosane;
1-chloro-30-iodotriacontane; and
1-chloro-40-iodotetracontane.

Products which can be made by the process of the present invention include, by way of example:
9-bromo-2-oxo-nonanoic acid;
10-bromo-oxodecanoic acid;
11-bromo-2-oxo-undecanoic acid;
12-bromo-2-oxo-dodecanoic acid;
13-bromo-2-oxo-tridecanoic acid;
14-bromo-2-oxo-tetradecanoic acid;
15-bromo-2-oxo-pentadecanoic acid;
16-bromo-2-oxo-hexadecanoic acid;
17-bromo-2-oxo-heptadecanoic acid;
18-bromo-2-oxo-octadecanoic acid;
19-bromo-2-oxo-nonadecanoic acid;
20-bromo-2-oxo-eicosanoic acid;
21-bromo-2-oxo-heneicosanoic acid;
22-bromo-2-oxo-docosanoic acid;
23-bromo-2-oxo-tricosanoic acid;

24-bromo-2-oxo-tetracosanoic acid;
25-bromo-2-oxo-pentacosanoic acid;
26-bromo-2-oxo-hexacosanoic acid;
27-bromo-2-oxo-heptacosanoic acid;
32-bromo-2-oxo-dotricontanoic acid;
42-bromo-2-oxo-dotetracontanoic acid;
9-chloro-2-oxo-nonanoic acid;
10-chloro-2-oxo-decanoic acid;
11-chloro-2-oxo-undecanoic acid;
12-chloro-2-oxo-dodecanoic acid;
13-chloro-2-oxo-tridecanoic acid;
14-chloro-2-oxo-tetradecanoic acid;
15-chloro-2-oxo-pentadecanoic acid;
22-chloro-2-oxo-docosanoic acid;
27-chloro-2-oxo-heptacosanoic acid;
32-chloro-2-oxo-dotricontanoic acid;
42-chloro-2-oxo-dotetracontanoic acid;
9-iodo-2-oxo-nonanoic acid;
10-iodo-2-oxo-decanoic acid;
11-iodo-2-oxo-undecanoic acid;
12-iodo-2-oxo-dodecanoic acid;
22-iodo-2-oxo-docosanoic acid;
27-iodo-2-oxo-heptacosanoic acid;
9-chloro-2-oxo-nonanoic acid;
10-chloro-2-oxo-decanoic acid;
11-chloro-2-oxo-undecanoic acid;
12-chloro-2-oxo-dodecanoic acid;
22-chloro-2-oxo-docosanoic acid;
27-chloro-2-oxo-heptacosanoic acid;
9-chloro-2-oxo-nonanoic acid;
10-chloro-2-oxo-decanoic acid;
11-chloro-2-oxo-undecanoic acid;
12-chloro-2-oxo-dodecanoic acid;
22-chloro-2-oxo-docosanoic acid;
27-chloro-2-oxo-heptacosanoic acid;
9-chloro-2-oxo-nonanoic acid;
10-chloro-2-oxo-decanoic acid;
11-chloro-2-oxo-undecanoic acid;
12-chloro-2-oxo-dodecanoic acid;
22-chloro-2-oxo-docosanoic acid; and
27-chloro-2-oxo-heptacosanoic acid;

The reaction is carried out in the presence of a mixture of water and alcohol as a reaction medium. Preferably, the alcohols employed for the reaction may be straight-chain, branched or cyclic, and preferably contain up to 6 carbon atoms. Methanol, ethanol, propanol, isopropanol, n-butanol, isobutanol, tert-butanol, and tert-amyl alcohol may be mentioned as examples. Cyclic ethers, such as tetrahydrofuran, also may be used. A particularly preferred solvent alcohol is tert-butanol. Mixtures containing about 10% to 90% by weight of water and about 90% to 10% by weight of alcohol generally are used. Preferred mixtures contain about 30% to 80% by weight water and about 70% to 20% by weight alcohol.

The reaction takes place in the presence of a basic substance suitably an alkali metal hydroxide or an alkaline earth metal hydroxide employing a metal carbonyl compound. During the reaction, the dihaloalkane undergoes reaction with the carbon monoxide and the basic substance whereby the desired halo-α-keto-carboxylic acid is formed.

Specific examples of suitable basic agents which can be used in the practice of the process include: LiOH, NaOH, KOH, RbOH, $Ca(OH)_2$, $Ba(OH)_2$ and $Mg(OH)_2$. LiOH and $Ca(OH)_2$ are particularly preferred.

The amount of basic agent used can vary within wide limits. In general, the molar ratio of the alkali metal base or alkaline earth metal base to dihaloalkane reactant is preferably 10:1 to 1:1.

In the process described herein, it is preferred to use metal carbonyl compounds as carbonylation catalysts. These catalysts include particularly metal carbonyls such as iron pentacarbonyl, dicobalt-octacarbonyl and nickel-tetracarbonyl, or their salts such as, for example, the calcium, potassium or sodium salts thereof. Dicobalt-octacarbonyl is very particularly suited. These catalysts can be added to the medium in the solid state or in the form of solutions in the solvent used for the carbonylation reaction. The molar percentage of the metal carbonyl compound to the dihaloalkane reactant is preferably from about 0.1 to about 25%.

The concentration of the dihaloalkane reactant used in the reaction solvent is not critical and can vary within wide limits. Thus, it can be between about 1 and 30% by weight, based on the weight of the solvent, however, it is possible to go outside of these limits without disadvantage.

The present process is advantageously carried out by bringing the mixture consisting of the dihaloalkane reactant, the metal carbonyl catalyst and the alkali metal base or the alkaline earth metal base, suspended in the mixture of water and alcohol, into contact, under nitrogen, in a suitable pressure-resistant reactor equipped with a stirrer, with a large excess of carbon monoxide (amount greater than 2 moles of carbon monoxide per mole of the starting dihaloalkane reactant) introduced at the desired pressure and temperature, in accordance with techniques suitable for bringing about the reaction between a liquid phase and a gas phase.

The carbonylation reaction is carried out at a temperature in the range of from about 30° C. to about 150° C., preferably from about 50° C. to 100° C. While the length of reaction time will vary in relation to the reaction temperature, in general, the reaction is conducted at the temperatures indicated for a period of time sufficient to form, as the predominant product, a halo-α-keto-carboxylic acid. For example, at a reaction temperature of approximately 90° C., a reaction time of approximately four and one-half hours was found to be sufficient to produce a 66% yield of 14,bromo-2-oxo-tetradecanoic acid from 1,12-dibromododecane as shown in Example 1, below.

In general, the reaction takes place at elevated carbon monoxide pressures which may range from about 300 psig to about 3000 psig. Preferably, the reaction takes place at a pressure in the range of about 500 psig to 1000 psig. The carbon monoxide may contain or be mixed with an inert gas, such as nitrogen.

On completion of the reaction, the product mixture is filtered, resulting in the alkali metal basic reagent or to the alkaline earth metal basic reagent being separated from the liquid reaction components as the main solid component. The desired halo-α-keto-carboxylic acid product is easily separated from the resultant reaction mixture by such means as distillation, extraction, crystallization or the like.

The following examples illustrate the invention.

EXAMPLE 1

A 300 mL autoclave was charged with 20 g (60.95 mmoles) of 1,2-dibromododecane and 105 mLs of t-BuOH. Next, 1.39 g (4.06 mmoles) of $Co_2(CO)_8$ were added under CO, and then a mixture of 17.78 g (240 mmoles) of lime and 45 mLs of H₂O were added. After 860 psi CO was charged to the autoclave, the reaction mixture was heated to 90° C. over a period of time of approximately 1 hour and the reaction mixture was maintained at that temperature for 3.5 hours. After suction filtration, the solid was rinsed three times with 20 mL portions of a 50:50 t-butanol/water solution and then acidified with 200 mLs of an aqueous solution of HCl containing 500 mmoles of HCl. The free acid was extracted with diethyl ether (3×50 mLs) to give 12.92 g of 14,bromo-2-oxo-tetradecanoic acid (66% yield).

Having described the process which Applicant regards as his invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

1. A process for the preparation of halo-α-keto-carboxylic acids which comprises reacting a dihaloalkane in a liquid solvent medium with carbon monoxide at an elevated temperature of 30°–150° C. and an elevated pressure of 300–3000 psig in the presence of a catalytic amount of a metal carbonyl compound and an alkali metal inorganic base or an alkaline earth metal inorganic base and forming as the primary product a halo-α-keto-carboxylic acid.

2. A process for the preparation of a halo-α-keto-carboxylic acid of the general formula

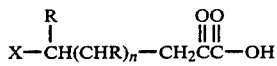

wherein R represents hydrogen or an alkyl radical which can be either straight chain or branched containing from 1–25 carbon atoms and n is 4 to 40, which comprises reacting a dihaloalkane of the general formula

wherein R and n are as defined above and X is the same or different halogen selected from chlorine, bromine or iodine, in a liquid solvent medium, with carbon monoxide at an elevated temperature of 30°–150° C. and an elevated pressure of 300–3000 psig in the presence of a catalytic amount of a metal carbonyl compound and an alkali metal inorganic base or an alkaline earth metal inorganic base and forming as the primary product of halo-α-keto-carboxylic acid.

3. The process of claim 2 wherein said dihaloalkane is 1,7-dibromoheptane, 1,8-dibromooctane, 1,9-dibromononane, 1,10-dibromodecane, 1,12-dibromododecane, 1,20-dibromoeicosane, 1,7-dichloroheptane, 1,8-dichlorooctane, 1,9-dichlorononane, 1,10-dichlorodecane, 1,12-dichlorododecane, 1,7-diiodoheptane, 1,8-diiodooctane, 1,9-diiodononane, 1,10-diiododecane, 1,12-diiodododecane, 1,20-diiodoeicosane, 1-chloro-7-bromoheptane, 1-chloro-8-bromooctane, 1-chloro-10-bromodecane, 1-chloro-7-chloroheptane, 1-chloro-8-chlorooctane, 1-chloro-10-chlorodecane, 1-chloro-8-iodooctane, 1-chloro-9-iodononane, or 1-chloro-10-iododecane.

4. The process of claim 2 wherein the products formed are 9-bromo-2-oxo-nonanoic acid, 10-bromo-2-oxodecanoic acid, 11-bromo-2-oxo-undecanoic acid, 12-bromo-2-oxo-dodecanoic acid, 13-bromo-2-oxo-tridecanoic acid, 14-bromo-2-oxo-tetradecanoic acid, 15-bromo-2-oxo-pentadecanoic acid, 16-bromo-2-oxo-hexadecanoic acid, 17-bromo-2-oxo-heptadecanoic acid, 18-bromo-2-oxo-octadecanoic acid, 19-bromo-2-oxo-nonadecanoic acid, 20-bromo-2-oxo-eicosanoic acid, 21-bromo-2-oxo-heneicosanoic acid, 22-bromo-2-oxo-docosanoic acid, 23-bromo-2-oxo-tricosanoic acid, 24-bromo-2-oxo-tetracosanoic acid, 25-bromo-2-oxo-pentacosanoic acid, 26-bromo-2-oxo-hexacosanoic acid, 27-bromo-2-oxo-heptacosanoic acid, 32-bromo-2-oxo-dotricontanoic acid, 42-bromo-2-oxo-dotetracontanoic acid, 9-chloro-2-oxo-nonanoic acid, 10-chloro-2-oxo-decanoic acid, 11-chloro-2-oxo-undecanoic acid, 12-chloro-2-oxo-dodecanoic acid, 13-chloro-2-oxo-tridecanoic acid, 14-chloro-2-oxo-tetradecanoic acid, 15-chloro-2-oxo-pentadecanoic acid, 9-iodo-2-oxo-nonanoic acid, 12-iodo-2-oxo-dodecanoic acid, 9-chloro-2-oxo-nonanoic acid, 10-chloro-2-oxo-decanoic acid, 12-chloro-2-oxo-dodecanoic acid, 9-chloro-2-oxo-nonanoic acid, 10-chloro-2-oxo-decanoic acid, 12-chloro-2-oxo-dodecanoic acid, 9-chloro-2-oxo-nonanoic acid, 10-chloro-2-oxo-decanoic acid or 12-chloro-2-oxo-dodecanoic acid.

5. The process of claim 3, wherein the carbon monoxide pressure is from about 500 to 1000 psig.

6. The process of claim 2, wherein the inorganic base is selected from LiOH, NaOH, KOH, RbOH, Ca(OH)₂, Ba(OH)₂ or Mg(OH)₂.

7. The process of claim 2, wherein the molar ratio of the inorganic base is from about 1 to 10 moles per mole of dihaloalkane reactant.

8. The process of claim 2, wherein the metal carbonyl catalyst compound is iron pentacarbonyl, dicobalt-octacarbonyl, or nickel-tetracarbonyl.

9. The process of claim 8, wherein the metal carbonyl is dicobalt-octacarbonyl.

10. The process of claim 8, wherein the metal carbonyl catalyst compound is a salt of iron pentacarbonyl, dicobalt-octacarbonyl or nickel-tetracarbonyl.

11. The process of claim 10, wherein said salt is sodium, potassium or calcium.

12. The process of claim 2, wherein the catalyst is formed by carbonylation in organic solvent and used in that solvent.

13. The process of claim 2, wherein the molar percentage of metal carbonyl compound to dihaloalkane reactant is from about 0.1 to about 25%.

14. The process of claim 2, wherein the liquid solvent medium is a mixture of water and alcohol.

15. The process of claim 14, wherein the mixture consists of from about 10% to about 90% by weight water and from about 90% to about 10% alcohol.

16. The process of claim 14, wherein the alcohol is a saturated, linear or branched, aliphatic, monohydroxylic or polyhydroxylic compound containing up to 6 carbon atoms.

17. The process of claim 16, wherein the alcohol is tert-butanol.

18. The process of claim 16, wherein the alcohol is isopropanol.

* * * * *

UNITED STATES PATENT AND TRADEMARK OFFICE
CERTIFICATE OF CORRECTION

PATENT NO. : 4,544,505
DATED : OCTOBER 1, 1985
INVENTOR(S) : JOACHIM W. WOLFRAM

It is certified that error appears in the above-identified patent and that said Letters Patent is hereby corrected as shown below:

Column 4, line 55, reads "10-bromo-oxodecanoic acid" and should read -- 10-bromo-2-oxo-decanoic acid --.

Column 5, line 22, reads "22-iodo-2-oxo-docosanoic acid;" and should read -- 22-iodo-2-oxo-docosanoic acid; and --.

Column 5, line 23, reads "27-iodo-2-oxo-heptacosanoic acid;" and should read --27-iodo-2-oxo-heptacosanoic acid. --.

Delete column 5, line 24 through column 5, line 42.

Column 8, line 23, reads "nonanoic acid, 12-iodo-2-oxo-dodecanoic acid, 9-" and should read -- nonanoic acid, or 12-iodo-2-oxo-dodecanoic acid. --.

Delete column 8, lines 24-29.

Column 8, line 30, reads "Claim 3" and should read -- Claim 2 --.

Signed and Sealed this

Twenty-first Day of January 1986

[SEAL]

Attest:

DONALD J. QUIGG

Attesting Officer

Commissioner of Patents and Trademarks